(12) United States Patent
Matsushita

(10) Patent No.: US 6,443,937 B1
(45) Date of Patent: *Sep. 3, 2002

(54) FASTENING SYSTEM FOR GARMENT

(75) Inventor: Michiyo Matsushita, Ehime-ken (JP)

(73) Assignee: Uni-Charm Corporation, Ehime-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/783,142

(22) Filed: Jan. 14, 1997

(30) Foreign Application Priority Data

Jan. 23, 1996 (JP) .............................................. 8-009003

(51) Int. Cl.[7] .......................... A61M 13/15; A61M 13/20
(52) U.S. Cl. ........................... 604/391; 664/386; 24/444
(58) Field of Search .......................... 604/386, 389–391; 24/306, 442–452; 128/DIG. 15

(56) References Cited

U.S. PATENT DOCUMENTS

| | | | | |
|---|---|---|---|---|
| 3,081,772 A | * | 3/1963 | Brooks et al. | 604/391 |
| 5,049,145 A | | 9/1991 | Flug | |
| 5,053,028 A | * | 10/1991 | Zoia et al. | 604/391 |
| 5,137,526 A | | 8/1992 | Coates | |
| 5,286,112 A | * | 2/1994 | Bible | 24/442 |
| 5,318,555 A | * | 6/1994 | Siebers et al. | 604/391 |
| 5,401,275 A | * | 3/1995 | Flug et al. | 604/391 |
| 5,545,159 A | * | 8/1996 | Lancaster et al. | 604/391 |
| 5,672,404 A | * | 9/1997 | Callahan, Jr. et al. | 604/391 |

FOREIGN PATENT DOCUMENTS

| | | |
|---|---|---|
| GB | 2284742 | 6/1995 |
| WO | 90/07313 | 7/1990 |

* cited by examiner

*Primary Examiner*—John G. Weiss
*Assistant Examiner*—K. M. Reichle
(74) *Attorney, Agent, or Firm*—Lowe Hauptman Gilman & Berner, LLP

(57) ABSTRACT

A fastening system for a garment such as a disposable diaper includes a hook panel having a plurality of hook elements and a loop panel having a plurality of loop elements. The hook panel includes a base panel having a top surface on which the hook elements extend and a back surface. The back surface of the base panel has a secured region and a non-secured region with respect to the garment. The non-secured region is defined toward one end from which the hook panel can be progressively released from the loop panel toward the other opposite end. The fastening system thereby reduces the chance that the hook panel might be readily and unintentionally released from the loop panel during use of the garment.

2 Claims, 4 Drawing Sheets

FASTENING SYSTEM FOR GARMENT

BACKGROUND OF THE INVENTION

The present invention relates to a fastening system for a garment and more particularly to an improved mechanical fastening system for a garment such as a disposable diaper, a diaper cover or incontinence pants.

As a fastening system for a garment of this type, a conventional tape or surface fastener comprises a combination of a hook panel and a loop panel respectively having a plurality of hook and loop elements (commonly known under the trade mark VELCRO TAPE or MAGIC TAPE). With this fastening system, hooks and loops of both panels extending substantially in vertical directions relative to the panels are brought into mechanical engagement as the hook panel and the loop panel contact one another.

FIGS. 5 and 6 are side view illustrations of a plurality of hook elements 17 on a hook panel 13 engaged with a plurality of loop elements 25 on a loop panel 14. Referring to FIG. 5, the hook panel 13 engages with the loop panel 14 as the hook panel is pressed on the loop panel in a direction indicated by arrow A and released therefrom as the hook panel is pulled vertically as indicated by arrow B. Referring now to FIG. 6, these two panels 13, 14 are tensioned, when they are pulled in horizontally opposite directions as indicated by arrows C, D from their mutually engaged states as illustrated by FIG. 5. FIG. 6 reveals that many of the hook elements 17 are positively brought into engagement with the corresponding loop elements 25. In the state illustrated by FIG. 5 on the other hand, the hook elements 17 are merely inserted into spaces defined among the loop elements 25 and only a few of the hook elements 17 are in engagement with the corresponding loop elements 25. As a consequence, the hook panel 13 can be easily released from the loop panel 14 as the hook panel 13 are pulled upward from the loop panel 14.

With respect to such a fastening system, Japanese Laid-Open Patent Application No. Hei4-276251 discloses that a loop panel may be intermittently bonded to a garment to facilitate many of the hook elements being caught by corresponding loop elements as a hook panel is horizontally pulled.

When a garment is placed on a wearer and fastened by engaging a hook panel with a loop panel of a fastening system, the hook panel is sometimes released from the loop panel due to a vertically oriented force carelessly exerted on the fastening system which tends to release the hook panel from the loop panel. To avoid such a situation, there is a demand for an improved fastening system such that, when a garment is placed on a wearer, a mutual engagement of these two panels cannot be easily released simply by an unintentional movement of the hook panel in the direction vertical to the loop panel but released only by positively pulling the hook panel in the vertical direction when it is desired to take off the garment from the wearer. While the previously mentioned Laid-Open Patent Application No. Hei4-276251 discloses a means ensuring that a hook panel and a loop panel be engaged with each other as the hook panel is moved in a horizontal direction relative to the loop panel, no means is disclosed by which an engagement of these two panels can be ensured as the hook panel is moved in the vertical direction relative to the loop panel.

SUMMARY OF THE INVENTION

In view of the problems as described above, it is a principal object of the invention to provide a fastening system for a garment to ensure that a hook panel is not easily released from a loop panel even if the hook panel is moved in a vertical direction away from the loop panel.

The object set forth above is achieved, according to the invention, by a fastening system attached to a waist region of a backsheet of a garment. The fastening system includes a pair of supporting tape members positioned at opposite side edges of the waist region. Each supporting tape member includes a top surface and has a first end secured to the corresponding side edge of the waist region and a second end extending outward beyond the corresponding side edge of the waist region. The fastening system further includes a pair of hook panels attached to the pair of supporting tape members, and a loop panel provided on an outer surface of the backsheet at a location appropriate for releasably engaging the pair of hook panels.

Each hook panel includes a base panel and a plurality of rows of hook elements. The base panel has a top surface and a back surface. A width of the base panel is defined by upper and lower side edges thereof in parallel with each other. The rows of hook elements extend vertically from the top surface of the base panel. The back surface of the base panel includes a secured region and a non-secured region. The secured region is secured by an adhesive agent applied over the full width thereof to the supporting tape and is outwardly adjacent to the first end of the associated supporting tape member. The non-secured region is not directly secured to the supporting tape and is outwardly adjacent the secured region and inwardly adjacent the second end of the associated supporting tape member. The hook elements are coextensive with the non-secured region wherein the number of the rows of the hook elements in the non-secured region is smaller than the number of the rows of the hook elements in the secured region.

In accordance with the present invention, each hook panel is capable of being progressively released from the loop panel by grasping the second end of the associated supporting tape member and pulling toward the first end of the associated suporting tape member. The rows of the hook elements in the non-secured region extend transversely of the direction in which the hook panel is progressively released from the loop panel. The hook elements which are coextensive with the non-secured region include from 2 to 20 rows of hook elements. A length of the non-secured region, as measured in the direction in which the hook panel is progressively released from the loop panel, is smaller than that of the secured region.

In accordance with a preferred aspect the present invention, the base panel has a bending resistance less than 0.1 g as measured by a stiffness tester available under the trademark GURLEY. Such a device is used in determination of all bending resistances disclosed in this application.

DESCRIPTION OF THE PREFERRED EMBODIMENT

A fastening system of the present invention used with a garment will be described in more detail with reference to the accompanying drawings of for a specific embodiment in which the fastening system is used with a disposable diaper, a typical example of the garment.

Figure 1:
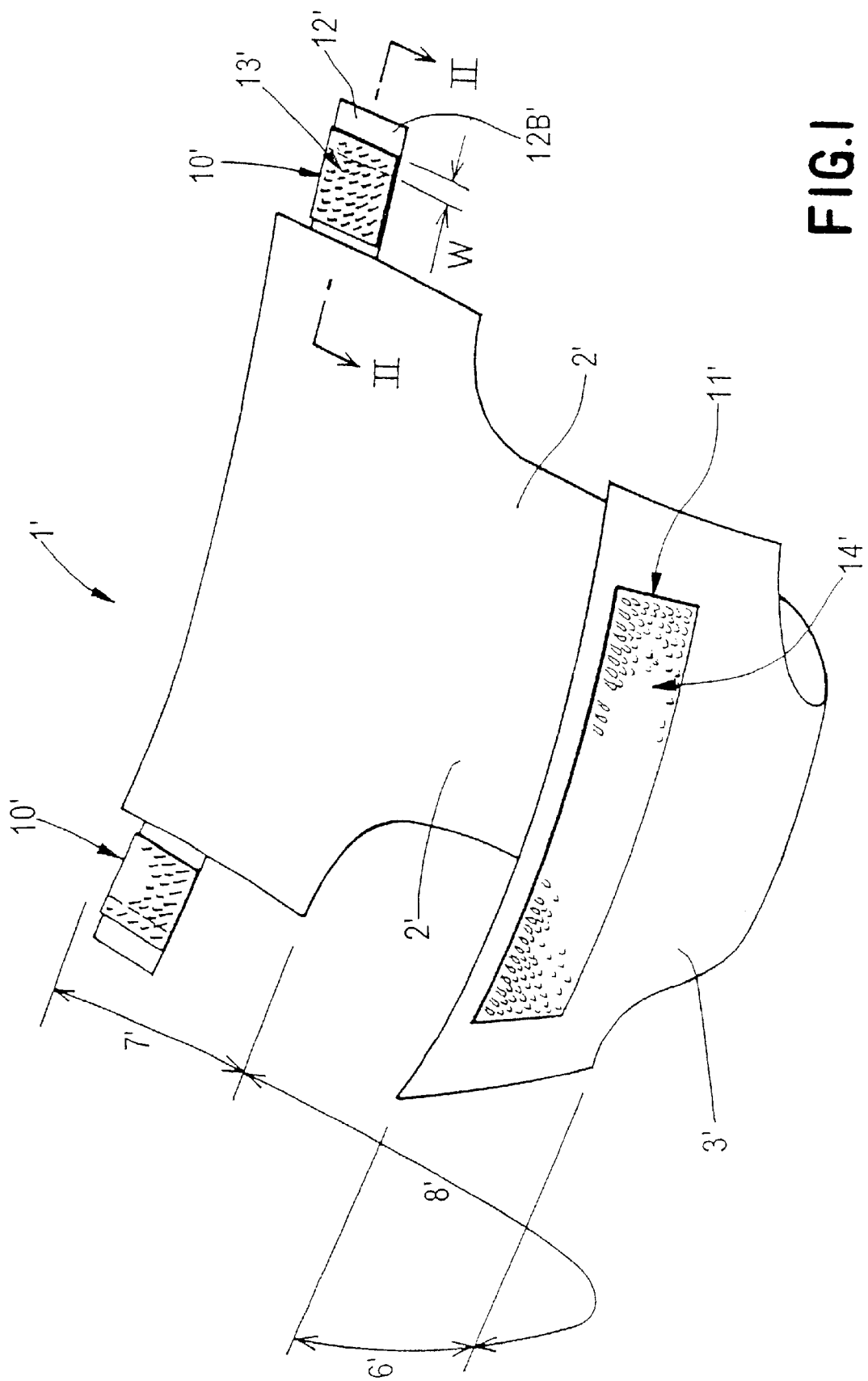
FIG. 1 is a perspective view of a disposable diaper provided with a fastening system of the invention.

A disposable diaper 1' shown by FIG. 1 in a perspective view comprises a liquid-permeable topsheet 2', a liquid-impermeable backsheet 3' and a liquid-absorbent core (not shown) disposed therebetween to define a front area 6', a rear area 7' and a crotch area 8' extending therebetween. The fastening system of the present invention comprises a fastening tape 10' and a receiving tape 11'. A pair of the fastening tapes 10' respectively extends from transversely opposite side edges of the rear waist region 7', and the receiving tape 11' is attached to an outer surface of the backsheet 3' and extends circumferentially.

Each of the fastening tapes 10' comprises a supporting tape 12' and a hook panel 13' secured to a top surface of the supporting tape 12'. The receiving tape 11' comprises a loop panel 14'. Hook panel 13' and loop panel 14' are commonly known under the trade mark VELCRO TAPE or MAGIC TAPE. Both panels 13', 14' cooperate with each other so that they are detachably fastened together to thereby reliably hold a diaper 1' on a wearer as the hook panel 13' is forced against the loop panel 14'.

To remove the diaper 1' from the wearer, an outer end 12B' of the supporting tape 12' is held by fingers of a person looking after the wearer. The hook panel 13' is progressively released from the loop panel 14' from the outer end 12B' toward an inner end 12A' opposed to the outer end 12B'.

Figure 2:
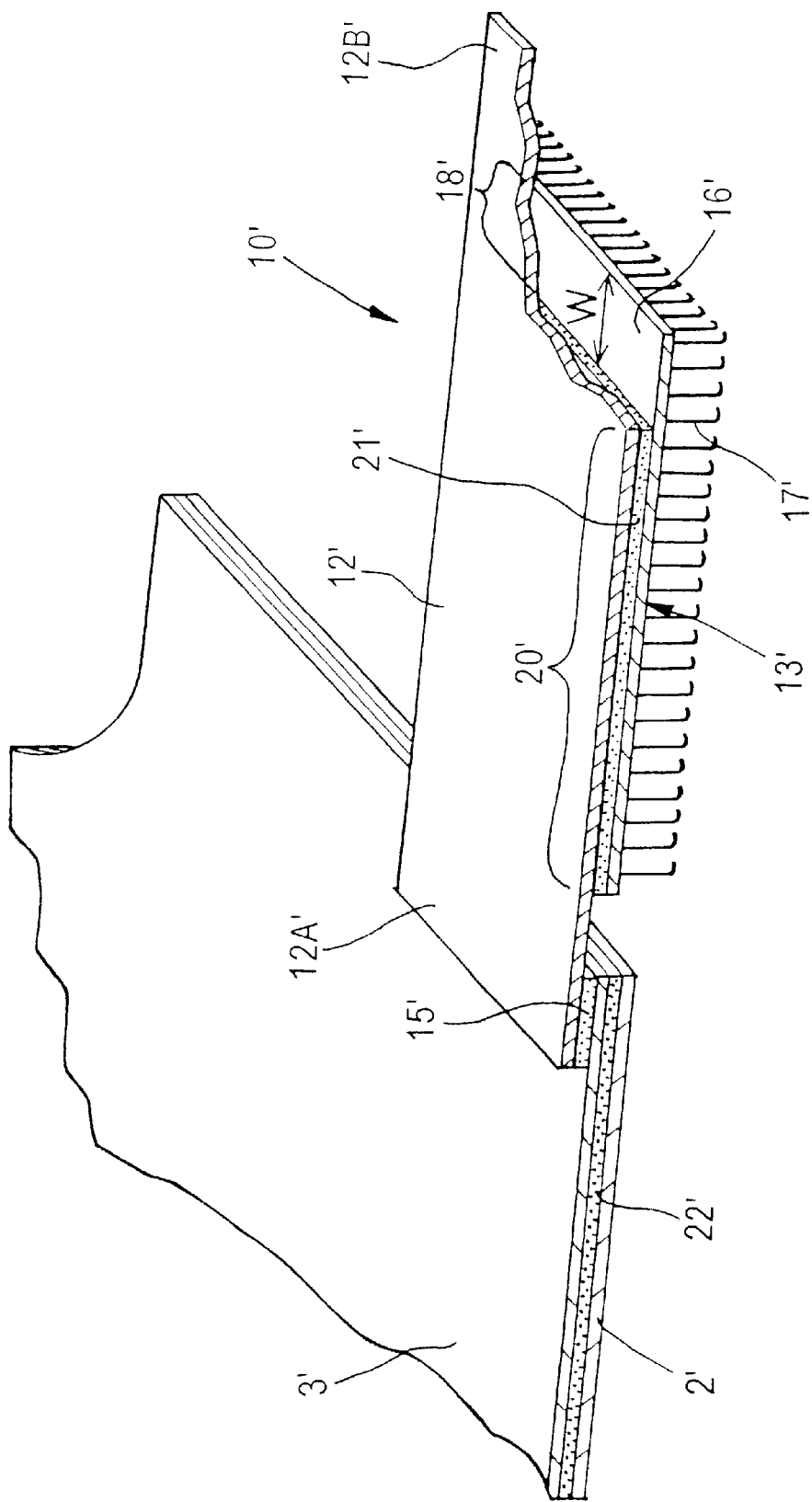
FIG. 2 is a fragmentary perspective view showing the fastening system as partially broken away when viewed in a direction indicated by arrows from a section taken along line II—II in FIG. 1

With reference to FIG. 2, the inner end 12A' of the supporting tape 12' is secured to an outer surface of the backsheet 3' by means of hot melt type adhesive 15'. The outer end 12B' serves as a grip zone used to release the fastening tape 10'. The hook panel 13' secured to a top or inner surface of the supporting tape 12' between the inner and outer ends 12A', 12B' comprises a base panel 16' and a plurality of hook elements 17' extending from the base panel in a vertical direction relative to the base panel. The base panel 16' is secured to the supporting tape 12' over a region 20' thereof except an outer end region 18' defined by a length W, and is fully secured over a width of the base panel 16' (refer also to FIG. 1) by means of hot melt type adhesive 21'. The outer end region 18' defines a non-secured zone with respect to the supporting tape 12'. 2–20 elements of the hook elements 17', preferably 5–15 elements of the hook elements 17', per 5 mm length are arranged on the base panel 16' longitudinally as well as transversely thereof and the outer end region 18' is provided with the hook elements 17' arranged in 2–20 rows, each extending transversely thereof. It should be understood that the topsheet 2' and the backsheet 3' are bonded together by means of hot melt adhesive 22' along transversely opposite side edges of the diaper 1'.

Figure 3:
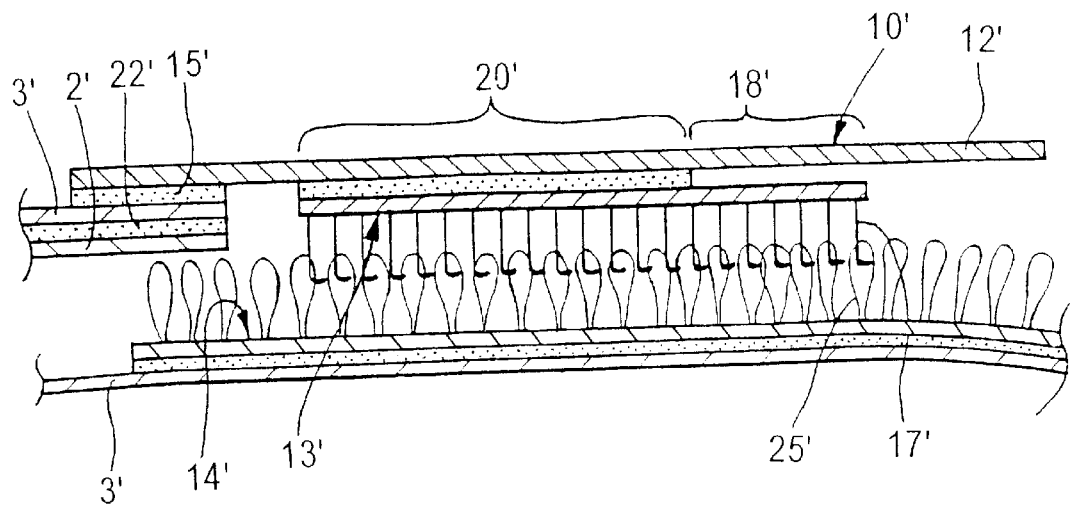
FIG. 3 is a side view showing a hook panel and a loop panel of the fastening system engaged with each other.
Figure 5:
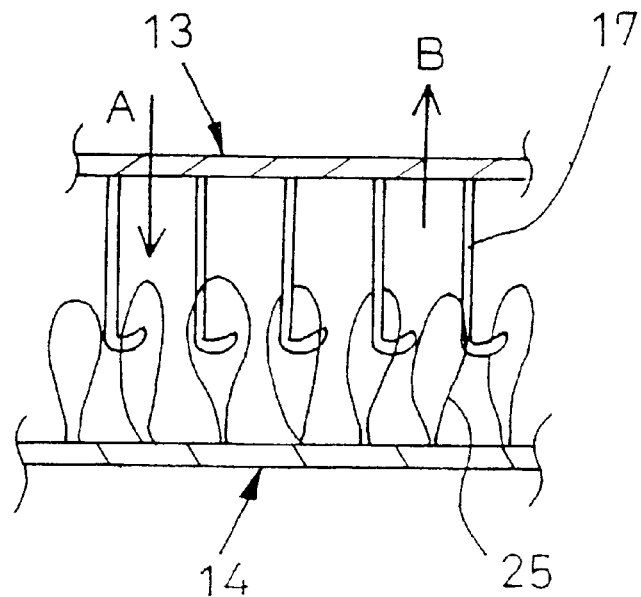
FIG. 5 is a fragmentary side view generally showing the state of a conventional hook panel and a conventional loop panel as they engage with each other.
Figure 6:
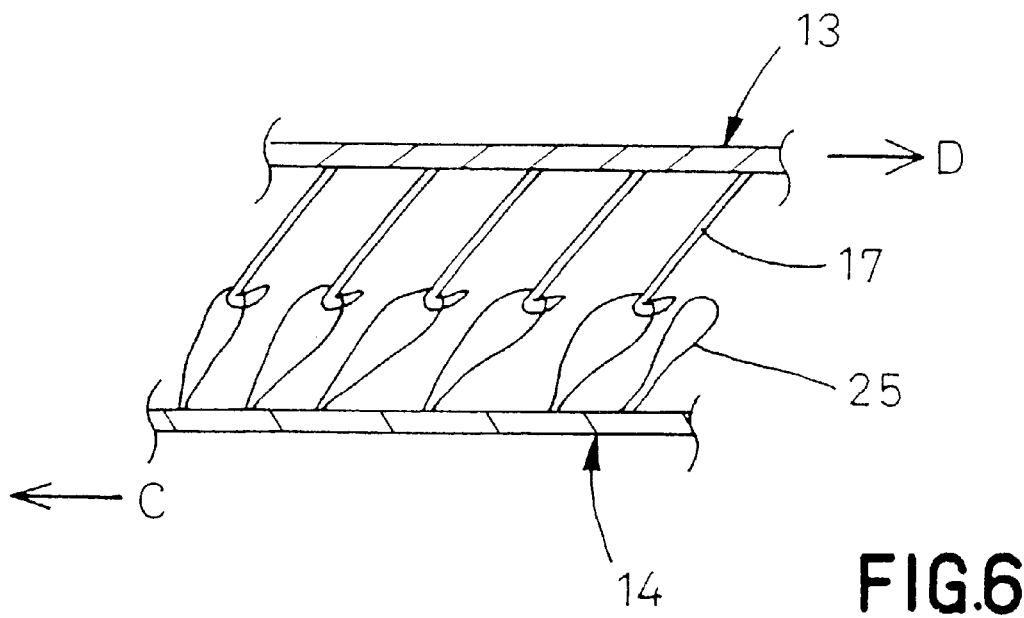
FIG. 6 is a fragmentary side view generally showing the state of the conventional hook and a loop panel as they are being pulled from their positions in FIG. 5 in horizontally opposite directions.

FIG. 3 is a side view similar to FIG. 5, illustrating a state in which the hook panel 13' is pressed in the vertical direction against the loop panel 14' having a plurality of loop elements 25' and brought into engagement with the loop panel 14'. In this state, a plurality of the vertically oriented hook elements 17' are merely inserted into spaces among a plurality of the loop elements 25'. The loop elements 25' are oriented in the substantially vertical direction and therefore a relatively small number of the hook elements 17' are effectively engaged with the correspondingly small number of the loop elements 25'.

Figure 4:
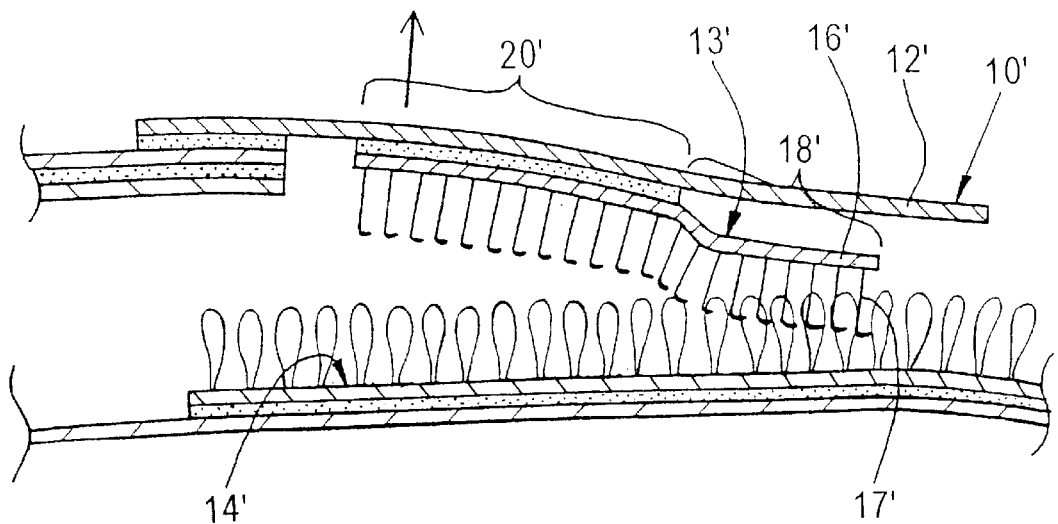
FIG. 4 is a side view showing the hook panel as it is being released from the loop panel.

FIG. 4 is a schematic diagram illustrating a state after the fastening tape 10' has moved upward in vertical direction from its position depicted in FIG. 3. As illustrated, the hook elements 17' follow the movement of the tape fastener 10' and smoothly leave the spaces defined among the loop elements 25' so far as the region 20' of the hook panel 13' bonded to the supporting tape 12' is concerned. In the outer end region 18' (nonsecured region), on the other hand, the movement of the fastening tape 10' causes the hook elements 17' to be tilted so as to be laterally brought into engagement with the corresponding loop elements 25' and thereby the hook panel 13' is prevented from being released away from the loop panel 14'. Obviously, the number of the rows of the hook elements 17' associated with the outer end region 18' of the base panel 16' is selected from a range of 2–20 rows, and accordingly the fastening tape 10' can be positively released from the receiving zone 11' without any difficulty.

Garments with which the fastening system of the present invention can be used include, in addition to the disposable diaper 1' illustrated as a typical example of the garments, diaper covers, incontinence pants, sanitary napkins, bandages and other various garments. The base panel 16' of the hook panel 13' preferably has a bending resistance less than 0.1 g as measured by a stiffness tester available under the trademark GURLEY. While the hook panel 13' has been described and illustrated as being attached to the diaper 1' with interposition of the supporting tape 12', it is also possible to attach the hook panel 13' directly to the diaper 1' at a desired location. Bonding or jointing of the diaper components, such as the hook panel 13' and the loop panel 14', may be achieved by utilizing, in addition to adhesive such as hot melt adhesive having appropriate softness, heat-sealing to the extent the components to be bonded are heat-sealable.

With the fastening system of the invention, there is no apprehension that the hook panel might be readily and unintentionally released from the loop panel even when the hook panel moves in the vertical direction away with respect to the loop panel with which the hook panel has been engaged. The outer end region of the hook panel is left as the non-secured region with respect to the supporting tape to which the remaining region of the hook panel is secured and the outer end region is provided with 2–20 rows of the hook elements.

What is claimed is:

1. A garment, comprising a backsheet and a fastening system attached to a waist region of the backsheet, the fastening system including:
   a pair of supporting tape members positioned at opposite side edges of the waist region, each supporting tape member including a top surface and a first end secured to the corresponding side edge of the waist region, and a second end extending outward beyond the corresponding side edge of the waist region;
   a pair of hook panels attached to the pair of supporting tape members, each said hook panel including:
      a base panel having a top surface and a back surface and a width of the base panel being defined by upper and lower side edges thereof in parallel with each other, and
      a plurality of rows of hook elements extending vertically from the top surface of said base panel, said back surface including a secured region secured by an adhesive agent applied over the full width thereof to the supporting tape and which is outwardly adjacent to said first end and a non-secured region which is not directly secured to the supporting tape and is outwardly adjacent said secured region and inwardly adjacent said second end, said hook elements being coextensive with said non-secured region wherein the number of the rows of the hook elements in the non-secured region is smaller than the number of the rows of the hook elements in the secured region; and a loop panel provided on an outer surface of the backsheet at a location appropriate for releasably engaging said pair of hook panels;

wherein said each hook panel is capable of being progressively released fiom the loop panel by grasping the second end of the associated supporting tape member and pulling toward the first end;

the rows of the hook elements in the non-secured region extend transversely of the direction in which the hook panel is progressively released from the loop panel;

said hook elements coextensive with said non-secured region include from 2 to 20 rows of hook elements; and a length of the non-secured region, as measured in the direction in which the hook panel is progressively released from the loop panel, is smaller than that of the secured region.

2. A garment, comprising a backsheet and a fastening system attached to a waist region of the backsheet, the fastening system including:

a pair of supporting tape members positioned at opposite side edges of the waist region, each supporting tape member including a top surface and a first end secured to the corresponding side edge of the waist region, and a second end extending outward beyond the corresponding side edge of the waist region;

a pair of hook panels attached to the pair of supporting tape members, each said hook panel including:

a base panel having a top surface and a back surface and a width of the base panel being defined by upper and lower side edges thereof in parallel with each other, and a plurality of rows of hook elements extending vertically from the top surface of said base panel, said back surface including a secured region secured by an adhesive agent applied over the full width thereof to the supporting tape and which is outwardly adjacent to said first end and a non-secured region which is not directly secured to the supporting tape and is outwardly adjacent said secured region and inwardly adjacent said second end, said hook elements being coextensive with said non-secured region wherein the number of the rows of the hook elements in the non-secured region is smaller than the number of the rows of the hook elements in the secured region and wherein the base panel has a bending resistance less than 0.1 g; and a loop panel provided on an outer surface of the backsheet at a location appropriate for releasably engaging said pair of hook panels;

wherein each said hook panel is capable of being progressively released from the loop panel by grasping the second end of the associated supporting tape member and pulling toward the first end;

said hook elements coextensive with said non-secured region include 2–20 rows of hook elements;

the rows of the hook elements in the non-secured region extend transversely of the direction in which the hook panel is progressively released from the loop panel; and a length of the non-secured region, as measured in the direction in which the hook panel is progressively released from the loop panel, is smaller than that of the secured region.

* * * * *